United States Patent
Hananel et al.

(10) Patent No.: US 10,639,503 B2
(45) Date of Patent: May 5, 2020

(54) HANDHELD DEVICES FOR PROJECTING FOCUSED ULTRASOUND AND RELATED METHODS

(71) Applicant: FusMobile Inc., Alpharetta, GA (US)

(72) Inventors: Ari Hananel, Alpharetta, GA (US); Ron Aginsky, Haifa (IL)

(73) Assignee: FusMobile Inc., Charlottsville, VA (US)

( * ) Notice: Subject to any disclaimer, the term of this patent is extended or adjusted under 35 U.S.C. 154(b) by 93 days.

(21) Appl. No.: 15/506,758

(22) PCT Filed: Aug. 26, 2015

(86) PCT No.: PCT/IL2015/050855
§ 371 (c)(1),
(2) Date: Feb. 27, 2017

(87) PCT Pub. No.: WO2016/030889
PCT Pub. Date: Mar. 3, 2016

(65) Prior Publication Data
US 2017/0246482 A1 Aug. 31, 2017

Related U.S. Application Data

(60) Provisional application No. 62/042,282, filed on Aug. 27, 2014.

(51) Int. Cl.
*A61N 7/02* (2006.01)
*A61B 90/00* (2016.01)
(Continued)

(52) U.S. Cl.
CPC ............ *A61N 7/02* (2013.01); *A61B 17/2251* (2013.01); *A61B 17/2258* (2013.01);
(Continued)

(58) Field of Classification Search
CPC .............. A61B 2090/376; A61B 90/37; A61B 2090/0811; A61B 2090/378; A61N 7/02
(Continued)

(56) References Cited

U.S. PATENT DOCUMENTS 5,285,772 A    2/1994 Rattner
5,350,351 A    9/1994 Saffer
(Continued)

FOREIGN PATENT DOCUMENTS

CN    100525722    8/2009
CN    102430211    5/2012
(Continued)

OTHER PUBLICATIONS

International Search Report of PCT Application No. PCT/IL2015/050855 dated Dec. 10, 2015.
(Continued)

*Primary Examiner* — Gary Jackson
*Assistant Examiner* — Zahed Kabir
(74) *Attorney, Agent, or Firm* — Pearl Cohen Zedek Latzer Baratz LLP

(57) ABSTRACT

Devices, systems, kits and methods are provided, that simplify focused ultrasound treatment. Devices comprise a supporting structure and a focused ultrasound (FUS) transducer having a central axis that is affixed to the supporting structure. Devices may further comprise an imaging ultrasound transducer and/or an x-ray aim, that may be attached to the supporting structure along the central axis of the FUS transducer. The FUS transducer is connected to a controller configured to control application of focused ultrasound by the transducer and may be associated with an imaging unit for imaging the treatment region using ultrasound and/or x-ray image data. The devices are hand held and easy to manipulate and aim correctly, utilizing coupling member(s)

(Continued)

as well as feedback from the concurrently imaged treatment region.

10 Claims, 13 Drawing Sheets

(51) Int. Cl.
*A61B 17/225* (2006.01)
*A61N 7/00* (2006.01)

(52) U.S. Cl.
CPC ........ *A61B 90/37* (2016.02); *A61B 2090/067* (2016.02); *A61B 2090/0811* (2016.02); *A61B 2090/376* (2016.02); *A61B 2090/378* (2016.02); *A61N 2007/0052* (2013.01); *A61N 2007/0095* (2013.01)

(58) Field of Classification Search
USPC .............................................................. 606/3
See application file for complete search history.

(56) References Cited

U.S. PATENT DOCUMENTS

| | | | |
|---|---|---|---|
| 5,388,581 A * | 2/1995 | Bauer | A61B 17/2255 378/162 |
| 7,305,264 B2 | 12/2007 | Larson et al. | |
| 7,553,284 B2 | 6/2009 | Vaitekunas | |
| 8,197,409 B2 | 6/2012 | Foley et al. | |
| 8,512,262 B2 | 8/2013 | Gertner | |
| 8,727,987 B2 | 5/2014 | Chauhan et al. | |
| 8,831,708 B2 | 9/2014 | Paladini et al. | |
| 9,161,735 B2 | 10/2015 | Bradford et al. | |
| 9,579,518 B2 | 2/2017 | Gertner | |
| 10,231,712 B2 | 3/2019 | Ebbini et al. | |
| 2002/0002345 A1 | 1/2002 | Marlinghaus | |
| 2005/0054955 A1 | 3/2005 | Lidgren | |
| 2005/0154308 A1 | 7/2005 | Quistgaard et al. | |
| 2007/0276243 A1 * | 11/2007 | Gerard | A61B 6/12 600/440 |
| 2007/0276297 A1 | 11/2007 | Fadler et al. | |
| 2008/0039746 A1 * | 2/2008 | Hissong | A61N 7/022 601/3 |
| 2009/0030308 A1 | 1/2009 | Bradford et al. | |
| 2010/0081893 A1 | 4/2010 | Jarvik et al. | |
| 2010/0210976 A1 | 8/2010 | Darlington | |
| 2010/0280420 A1 | 11/2010 | Barthe et al. | |
| 2011/0201929 A1 | 8/2011 | Vaezy et al. | |
| 2012/0121068 A1 * | 5/2012 | Maurer, Jr. | A61B 6/00 378/62 |
| 2012/0238919 A1 | 9/2012 | Gertner | |
| 2013/0144165 A1 | 6/2013 | Ebbini et al. | |
| 2014/0018708 A1 | 1/2014 | Dunbar et al. | |
| 2015/0294454 A1 * | 10/2015 | Nempont | A61B 6/12 382/128 |

FOREIGN PATENT DOCUMENTS

| | | |
|---|---|---|
| CN | 102781516 | 11/2012 |
| DE | 4302538 C1 | 4/1994 |
| DE | 102010018857 A1 | 12/2010 |
| EP | 0627206 A2 | 12/1994 |
| EP | 2332614 A1 | 6/2011 |
| FR | 2827149 A1 | 1/2003 |
| JP | H2-114953 | 4/1990 |
| JP | H3-141938 | 6/1991 |
| JP | H8-131454 | 5/1996 |
| JP | H9-164137 | 6/1997 |
| JP | 2012-239791 | 12/2012 |
| JP | 2013-505789 | 2/2013 |
| WO | WO/2007140331 | 12/2007 |
| WO | WO 2008/118300 A1 | 10/2008 |
| WO | WO 2010/009141 | 1/2010 |
| WO | WO/2013048912 | 4/2013 |
| WO | WO 2013/128349 | 9/2013 |
| WO | WO 2013128349 | 9/2013 |
| WO | WO 2014/160964 | 10/2014 |
| WO | WO 2014193013 | 12/2014 |

OTHER PUBLICATIONS

European Search Report of Application No. 19160576.5 dated Jun. 26, 2019.
Japanese Office Action of Application No. 2017-530452 dated Jun. 4, 2019.
Chinese Office Action of Application No. 2015800580387 dated Oct. 15, 2018.

* cited by examiner

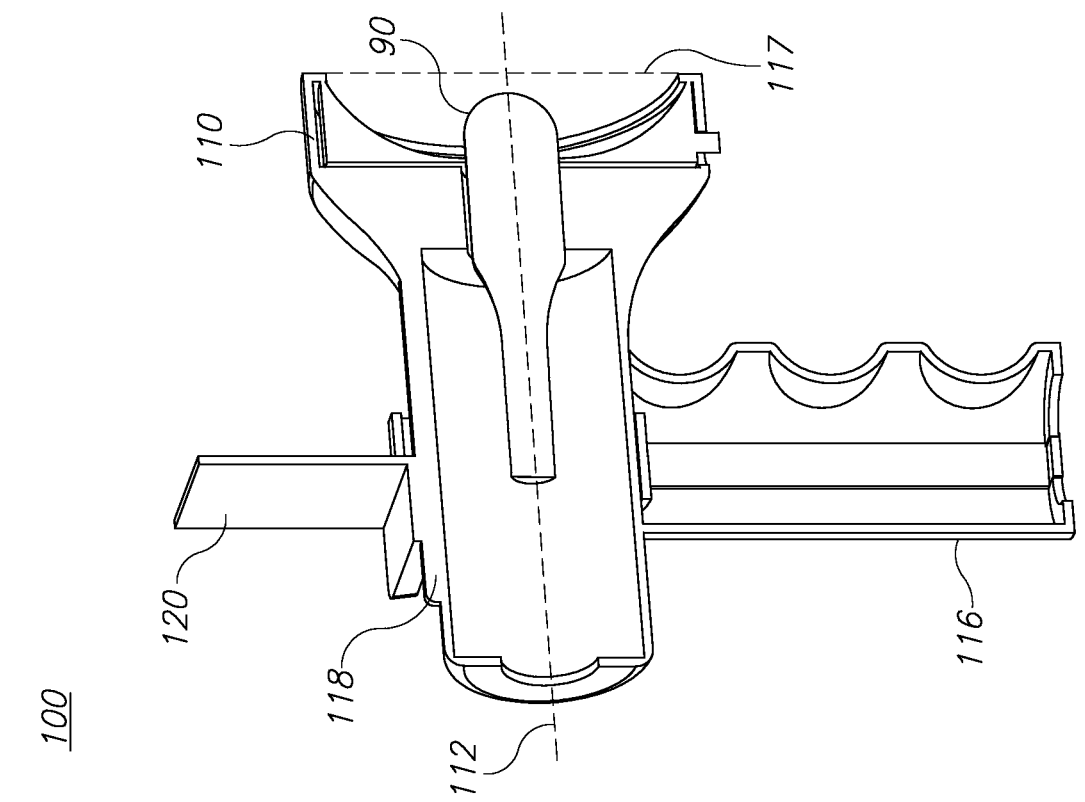
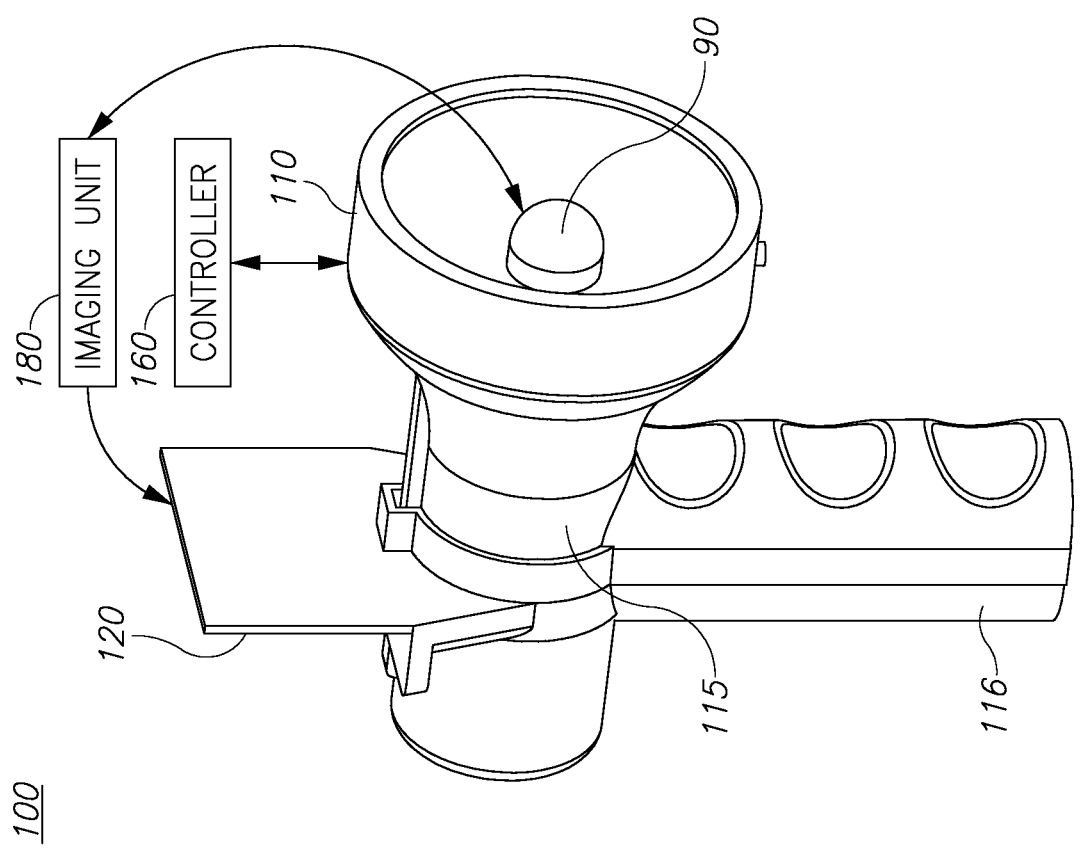

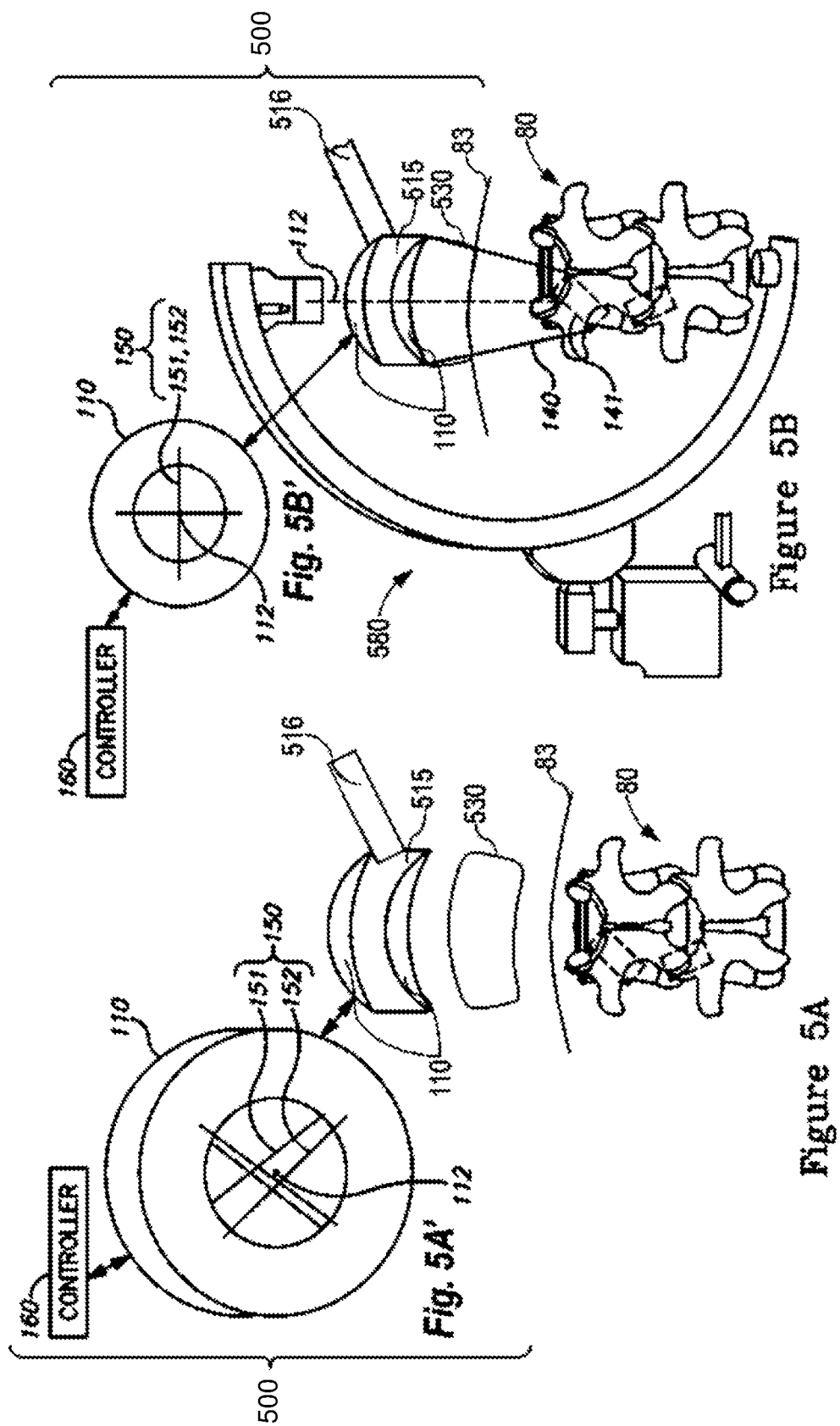

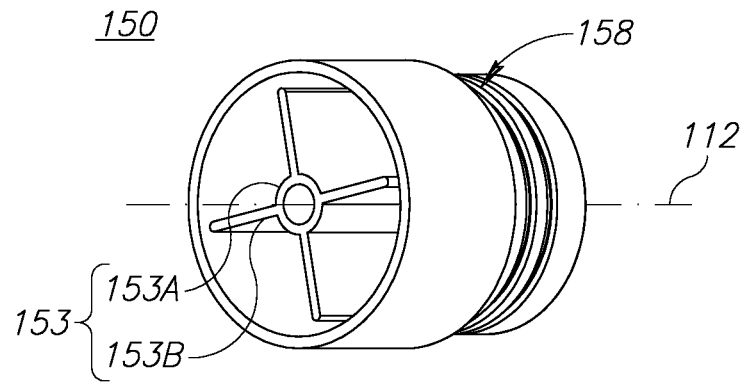
Figure 6A
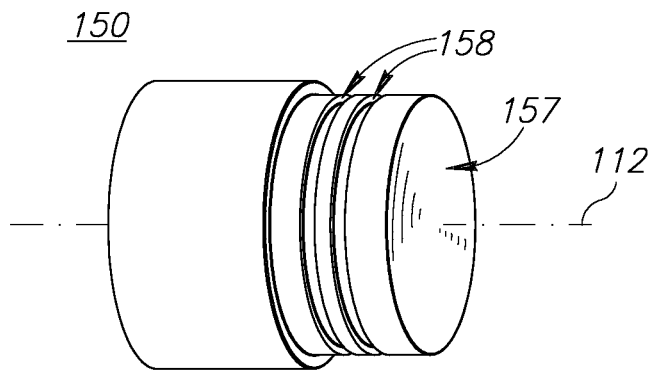
Figure 6B
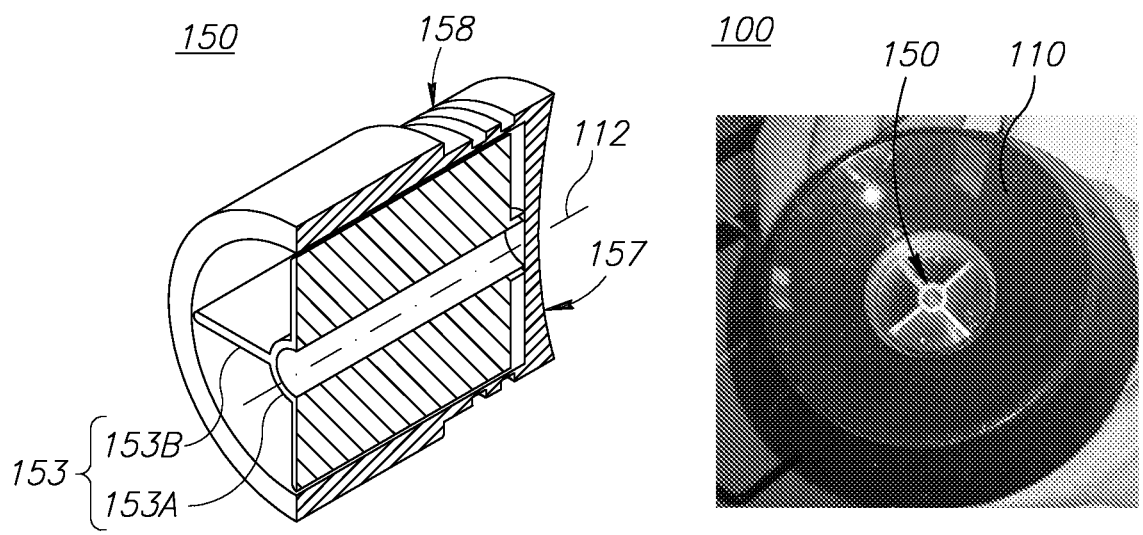
Figure 6C
Figure 6D

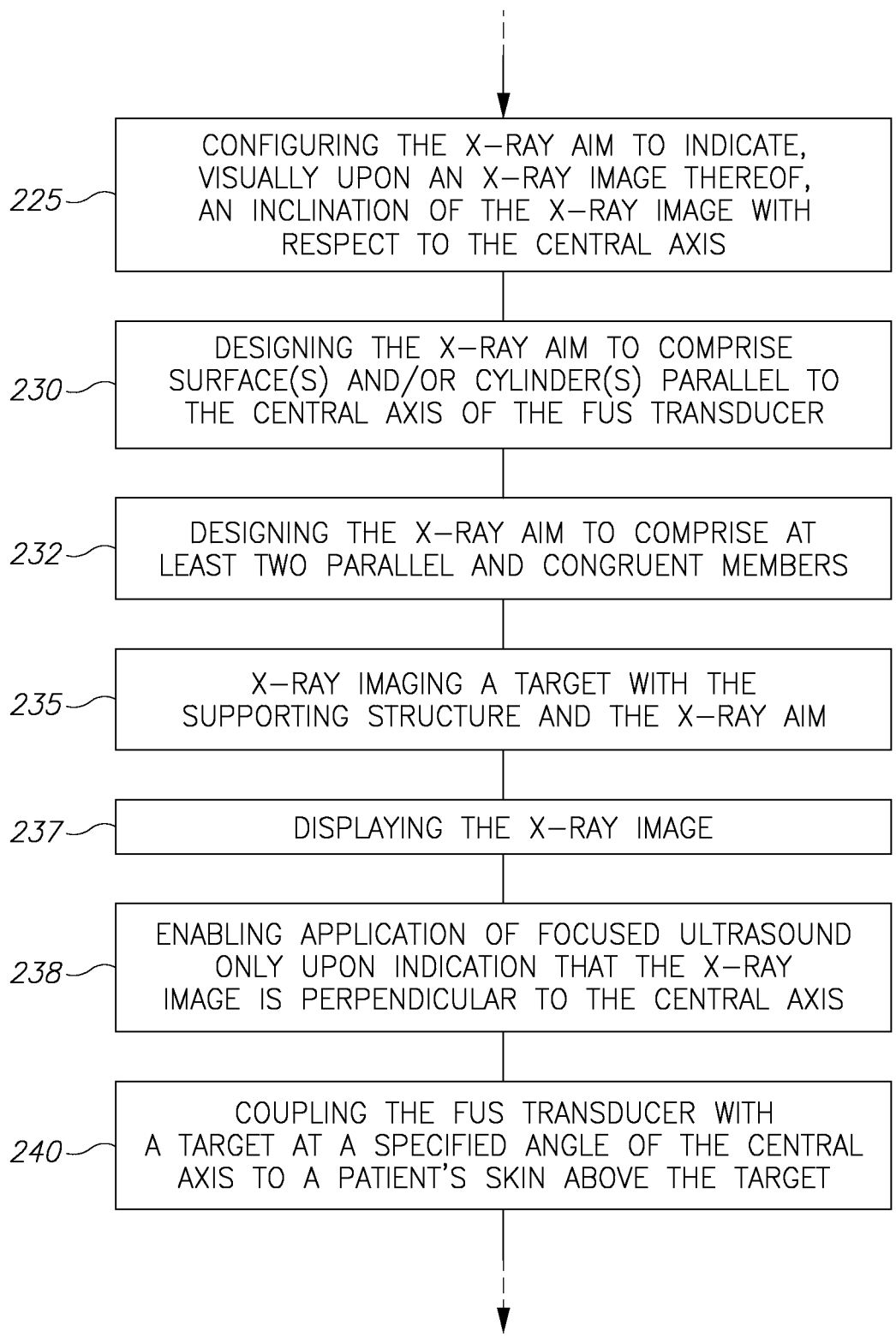
Figure 9 (cont. 1)

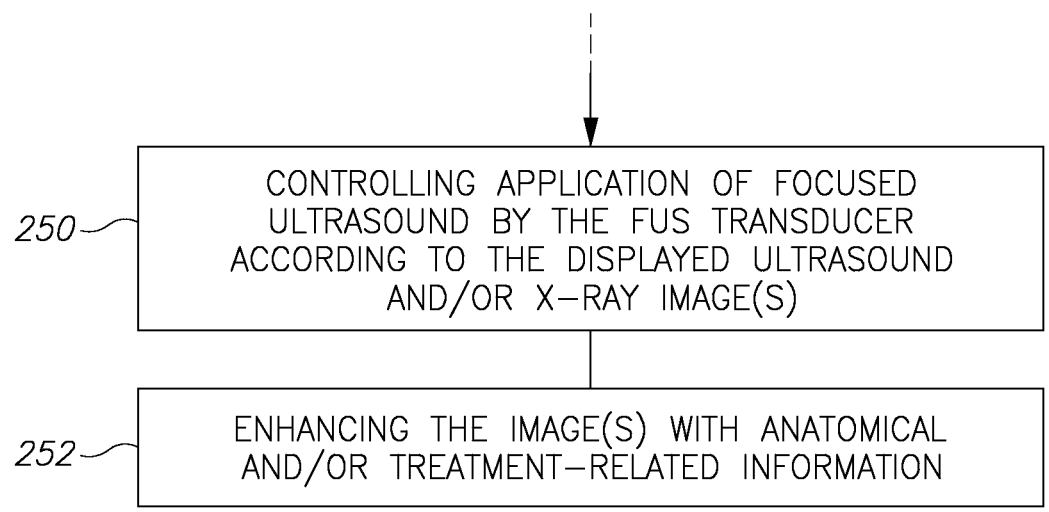
Figure 9 (cont. 2)

HANDHELD DEVICES FOR PROJECTING FOCUSED ULTRASOUND AND RELATED METHODS

CROSS-REFERENCE TO RELATED APPLICATIONS

This application is a National Phase Application of PCT International Application No. PCT/IL2015/050855, International Filing Date Aug. 26, 2015, claiming priority of U.S. Patent Application No. 62/042,282, filed Aug. 27, 2014, which is hereby incorporated by reference.

BACKGROUND OF THE INVENTION

1. Technical Field

The present invention relates to the field of focused ultrasound (FUS), and more particularly, to a handheld, imaging enabled, FUS device providing an intuitive interface.

2. Discussion of Related Art

Focused ultrasound may be applied to treat a variety of conditions by delivering focused acoustic energy to the treatment location. For example, in facet rhizotomy, medial nerve branches in the spine are ablated to treat facet-joint-related neck and back pain by denervation.

U.S. Pat. No. 7,305,264, which is incorporated herein by reference in its entirety, teaches transcutaneous application of planar or focused ultrasound to reduce bone pain of skeletal metastases in cancer patients. X-Ray or ultrasound imaging may be used to locate and display the therapeutic target site and planar or focused ultrasound may be applied at frequencies between 0.75 and 7.0 MHz using e.g., a gel couplant. The imaging and therapy transducers used to treat the nerves may be separate units, but connected by a rigid construction or the imaging and therapy transducers may be incorporated into a single unit, so that imaging and therapy can be accomplished with the same electronic control interface.

U.S. Patent Publication No. 2014/0018708, which is incorporated herein by reference in its entirety, teaches real-time, image-guided high intensity focused ultrasound targeting and treatment of tissue. Image guidance may comprise three-dimensional visualization of the tissue using an ultrasound imaging device, depicting a real-time image plane parallel to a feature of the applicator and an active orthogonal frame depicting a real-time image plane orthogonal to the active parallel plane. The ultrasound imaging component may be configured to undock from the system for use as a stand-alone ultrasound imaging device U.S. Pat. No. 7,553,284 teaches using focused ultrasound for pain reduction after nerve stimulation by applying a lower ultrasound level.

U.S. Patent Publication No. 2005/0154308, which is incorporated herein by reference in its entirety, teaches a disposable transducer seal designed to seal an open aperture of a transducer housing for a therapeutic ultrasound procedure.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a device comprising a supporting structure, a focused ultrasound (FUS) transducer having a central axis that is affixed to the supporting structure, and an imaging ultrasound transducer attached to the supporting structure along the central axis of the FUS transducer, wherein the FUS transducer is connected to a controller configured to control application of focused ultrasound by the transducer and the imaging transducer is connected to an imaging unit configured to derive imaging data from the imaging transducer.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIGS. 1A and 1B are high level schematic illustrations of a device, according to some embodiments of the invention.

FIGS. 6A-6D are high level schematic illustrations of an x-ray aim, according to some embodiments of the invention.

DETAILED DESCRIPTION OF THE INVENTION

Figure 2:
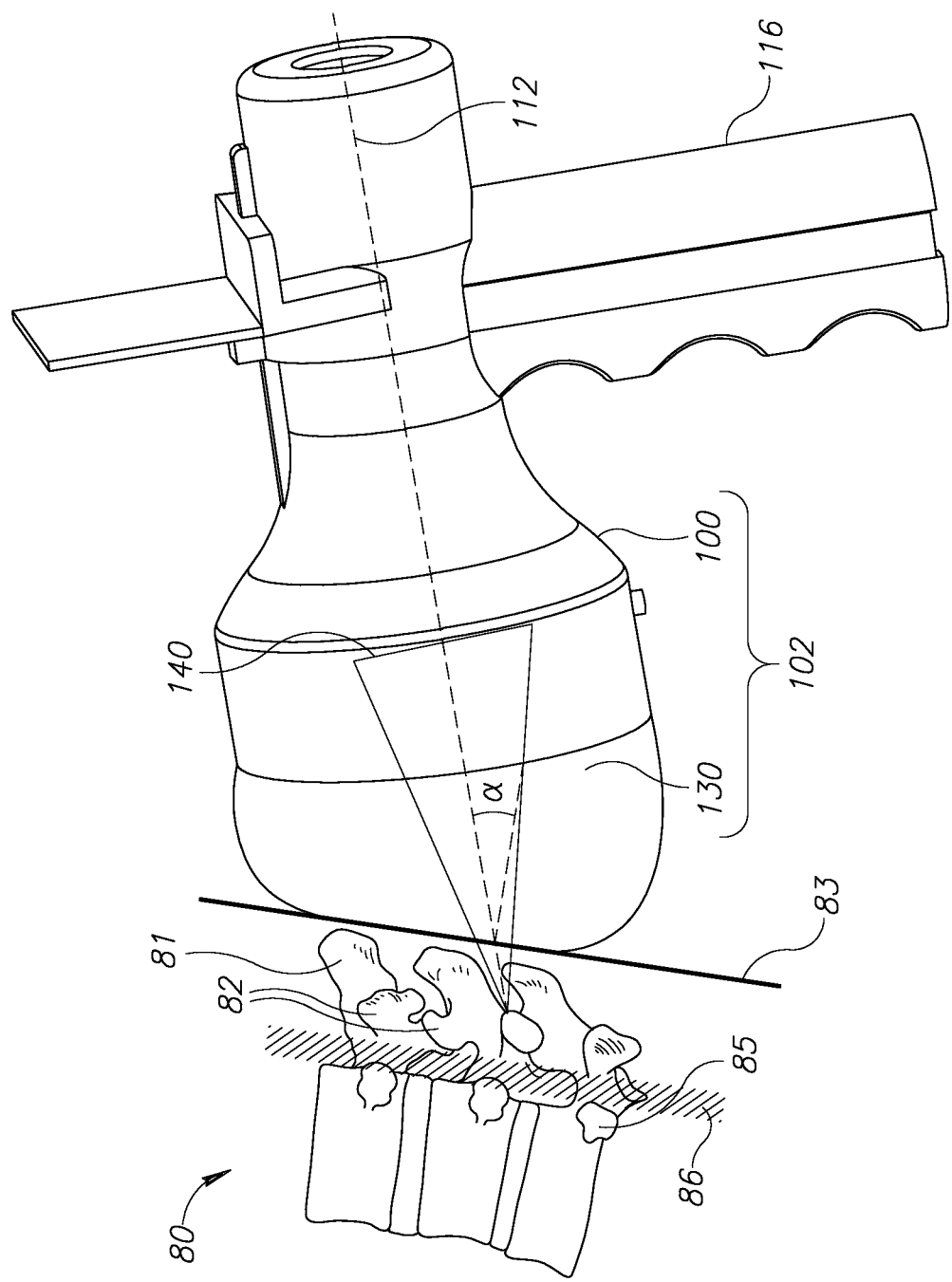
FIG. 2 is a high level schematic illustration of device applications, according to some embodiments of the invention.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Devices, systems, kits and methods are provided, that simplify focused ultrasound treatment. Devices comprise a supporting structure and a focused ultrasound (FUS) transducer having a central axis that is affixed to the supporting structure. Devices may further comprise an imaging ultrasound transducer and/or an x-ray aim, that may be attached to the supporting structure along the central axis of the FUS transducer. The FUS transducer is connected to a controller configured to control application of focused ultrasound by the transducer and may be associated with an imaging unit for imaging the treatment region using ultrasound and/or x-ray image data. The devices are hand held and easy to manipulate and aim correctly, utilizing coupling member(s) as well as feedback from the concurrently imaged treatment region.

FIGS. 1A and 1B are high level schematic illustrations of a device 100, according to some embodiments of the invention. Device 100 comprises a supporting structure 115 (such as a handheld frame), a focused ultrasound (FUS) transducer 110 having a central axis 112 that is affixed to supporting structure 115, and an imaging ultrasound transducer 90 attached to supporting structure 115 along central axis 112 of FUS transducer 110. FUS transducer 110 may be connected to a controller 160 configured to control application of focused ultrasound by FUS transducer 110 and imaging transducer 90 may be connected to an imaging unit 180 configured to derive imaging data from imaging transducer 90. For example, FUS transducer 110 may be applied to yield therapeutic results.

In certain embodiments, supporting structure 115 may be configured to enable use of standard imaging transducers 90 and/or enable replacement of imaging transducer 90. Supporting structure 115 may comprise a handle 116 (such as a hand grip, possibly perpendicular to central axis 112) and may be configured to provide simple intuitive manipulation of transducers 110, 90 to enable effective and flexible treatment by focused ultrasound that is based on ultrasound imaging.

Focused ultrasound (FUS) transducer 110 such as a FUS energy projector may be attached to supporting structure 115 such as a handheld frame to transmit an ultrasonic therapeutic energy beam to a treatment location within a target patient. FUS transducer 110 may be mechanically connected to supporting structure 115 in a way that sets a focal spot location of FUS transducer 110 along central axis 112 and in the center of the field of view of ultrasound imaging transducer 90. Supporting structure 115 may be configured to enable simultaneous tilting of display 120, FUS transducer 110 and imaging transducer 90, e.g., by a single hand maneuver, while maintaining the transducers centered along the (now tilted) central axis 112 and hence provide intuitive operation of device 100. Device 100 may be configured to enable single-handed focused ultrasound application.

Supporting structure 115 may further comprise a display 120 that is connected to imaging unit 180 and configured to display the imaging data from imaging unit 180. It is noted that display 120 may be mounted on supporting structure 115 in a way that simplifies the aiming of focused ultrasound on targets that are imaged by imaging ultrasound transducer 90, and/or may be separate from supporting structure 115 and comprise e.g., a screen or a computer display that may be used by the operator to achieve higher magnifications and enable further processing. Combinations of mounted display 120 and separate display 120 are likewise embodiments of the present invention.

In certain embodiments, device 100 may further comprise a mechanical shutter 117 (illustrated schematically by the broken line in FIG. 1B) that is attached to supporting structure 115 in front of imaging transducer 90 and is configured to protect imaging transducer 90 during an operation of FUS transducer 110. Alternatively or complementarily, protection of imaging transducer 90 during an operation of FUS transducer 110 may be carried out electronically.

In certain embodiments, FUS transducer 110 may be operated in a phased array technology and the treatment location may be adjusted along central axis 112. In certain embodiments, FUS transducer 110 may comprise a single element transducer or a high intensity transducer with a natural focus. FUS transducer 110 may be annular (ring-shaped) and have its focus position along central axis 112. Annular FUS transducer 110 may be selected to balance the configurability and complexity of phased array transducer with the simplicity and limitations of single element transducers, leaving one degree of freedom (depth along central axis 112) to be adjusted during the treatment.

FIG. 2 is a high level schematic illustration of device applications, according to some embodiments of the invention. Patient's tissue 80 is illustrated as including the patient's vertebral column below skin 83, and specifically the vertebra parts: spinous processes 81, transverse processes 85 and superior and inferior articular processes 82 (the sliding joints between these respective processes is termed the facet joint, and it is usually associated with two respective nerves); as well as spinal cord 86 are illustrated schematically. In certain embodiments, device 100 may be part of a kit 102 that further comprises a coupling member 130 configured to couple transducers 110, 90 with a target such as a patient's body part at a specified angle $\alpha$ with respect to central axis 112. Coupling member 130 may e.g., be wedge-shaped with wedge angle $\alpha$ or be deformable to enable modifying and adjusting angle $\alpha$. In certain embodiments, coupling member 130 may be designed to mimic the inner shape of transducers 110 and/or 90 in order to enhance the coupling quality to the transducers. In certain embodiments, coupling member 130 may be a deformable gel pad. Coupling member 130 may be configured as an ultrasound energy waveguide configured to guide an angled transmission of the ultrasound treatment energy beam from FUS transducer 110 to treatment location 141. In certain embodiments, coupling member 130 may be attached to the front of device 100 by any type of attachment (e.g., mechanically such as by a clip, a ring, an elastic band, a sheet, etc., pneumatically, adhesively, shape-induced etc.). In certain embodiments, coupling member 130 may be between 5-120 mm thick and be wedge-shaped with angle $\alpha$ in the range 0-80°, or in the range 30-60°. Coupling member 130 may be flexible (enable its configuration in at least two angles and/or thicknesses) and configured to enable angle adjustment by pressing device 100 against coupling member 130 supported by a patient's skin 83 of a respective patient's tissue 80, as illustrated schematically in FIG. 2. Coupling member 130 may be configured to define an acoustic pathway for energy beam 140 to reach treatment location 141 such as a facet joint nerve, at a specified spatial relation to the patient's anatomy and posture to reduce the risk of damage to a non-targeted tissue such as the nerve root and/or spinal cord by blocking the energy via the absorption by the vertebral bone tissue.

Coupling member 130 may be used to modify the position of the treatment location, specifically with respect to ultrasound reflections off surrounding bones (e.g., vertebra and vertebra processes). Angle α may be selected to increase the energy beam absorption by the bone tissue adjacent to the target nerve as well as to reduce the possibility of damage to sensitive non-targeted tissue such as the nerve root and/or spinal cord. For example, angle α may be selected to provide protection of the nerve roots and spinal cord from accidental damage by the energy beam, by shielding them by vertebral bone (e.g., by specific vertebra processes and vertebra lamina). In a non-limiting illustrational example, the vertebra processes may allow a 40° access angle to the treatment location from the vertical to the skin and the depth to the treatment location may be 5 cm. Coupling member 130 may be selected or adjusted to position device 100 at a corresponding energy delivery location, from which ultrasound energy may be focused at the defined treatment location. In certain embodiments, kit 102 may comprise a plurality of gel pads having different fixed thicknesses, e.g., ranging between 5-120 mm and having one or more different angles. In certain embodiments, kit 102 may comprise one or more flexible coupling members 130 such as gel-filled balloons of different dimensions, balloons filled with cold degassed water, flexible membranes filled with water or other fluid, gel or fluid filled pads etc. Coupling member 130 may be configured to further focus, to deflect or to spread focused ultrasound beam 140. Coupling member 130 may be configured as a disposable element.

Figure 3A:
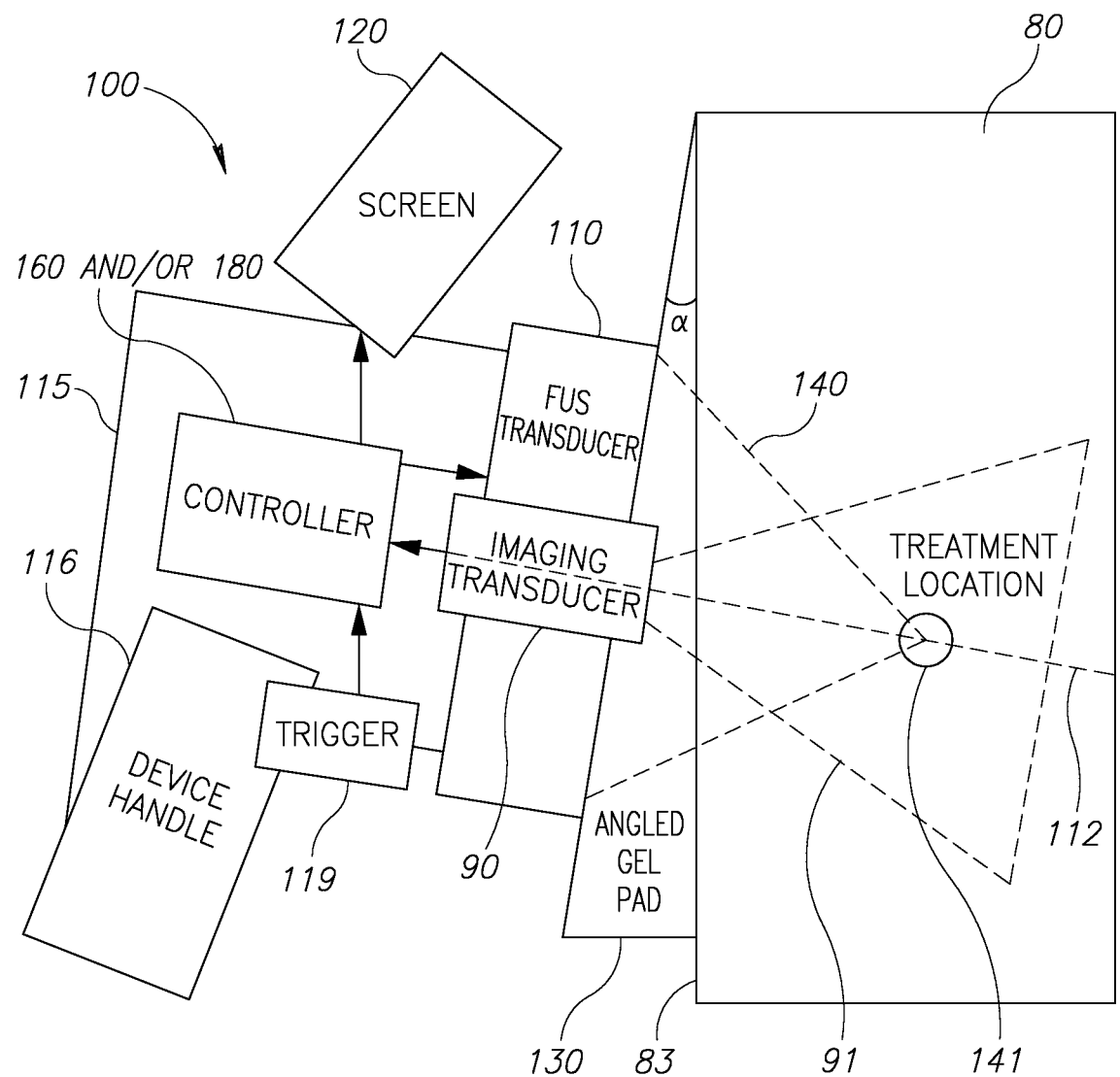
FIG. 3A is a high level schematic illustration of device units, according to some embodiments of the invention.
Figure 3B:
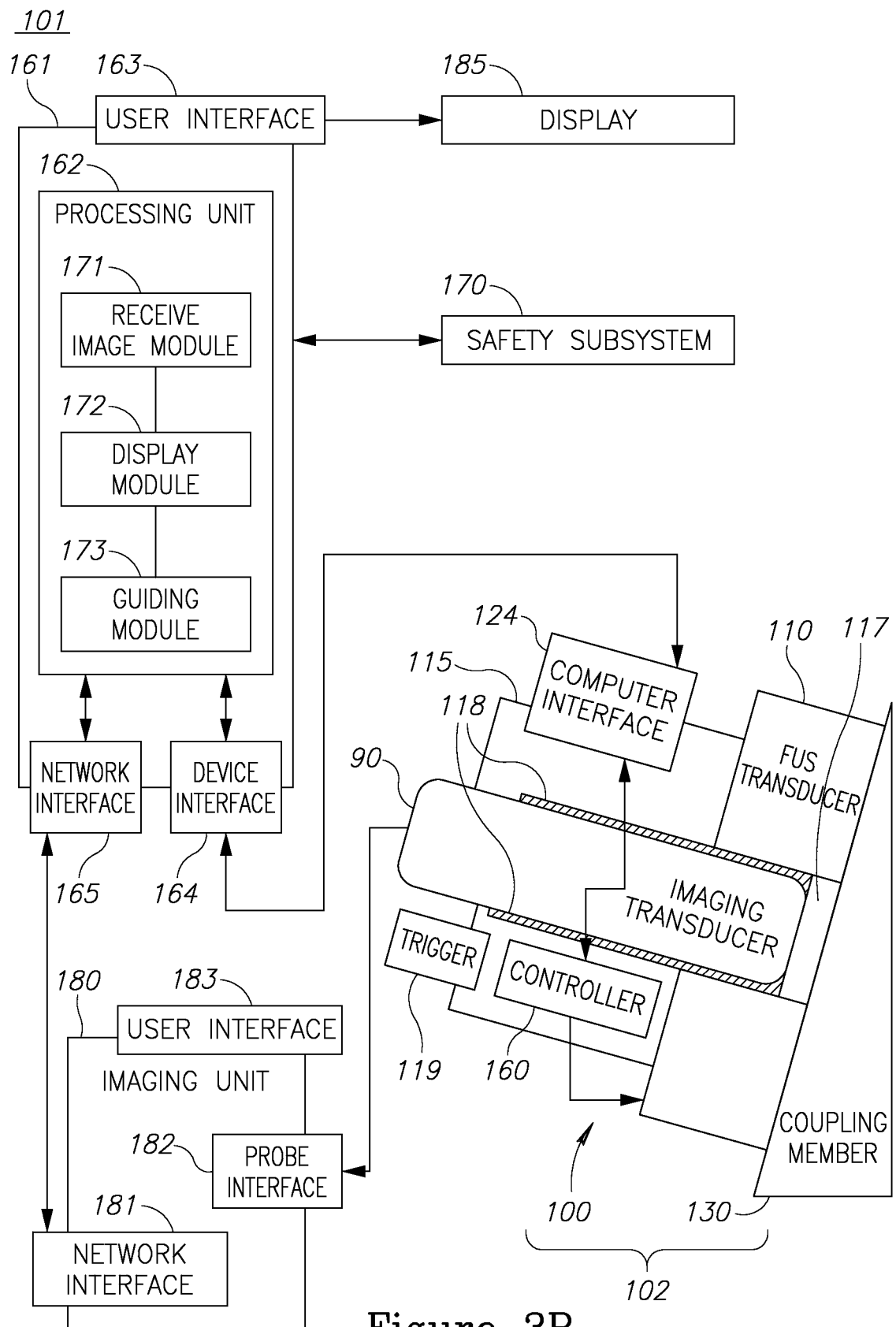
FIG. 3B is a high level schematic illustration of a system comprising the device, according to some embodiments of the invention.

FIG. 3A is a high level schematic illustration of device units, according to some embodiments of the invention. FIG. 3B is a high level schematic illustration of a system 101 comprising device 100, according to some embodiments of the invention.

FIG. 3A schematically illustrates conceptual configurations of device 100, including FUS transducer 110 having imaging transducer 90 at its center, coupled via coupling member 130 to tissue 80. Imaging transducer 90 may be configured to image a region 91 of tissue 80 that includes a treatment location 141 before, during and/or after treatment. Ultrasound imaging may be carried out at a fixed or at an adjustable imaging plane that may include treatment location 141. FUS transducer 110 may be configured to focus and deliver ultrasound energy 140 to treatment location 141, both at the angle α defined by coupling member 130 that is placed at patient's skin 83. FUS transducer 110 is configured to project acoustic energy 140 in a focused manner onto treatment location 141 as the focal spot location, possibly utilizing adjacent bone structures and avoiding damage to adjacent soft tissues.

For example, device 100 and angle α may be configured to yield a spatial position of treatment location 141 along central axis 112 of FUS transducer 110 and at a center of the imaging plane of imaging transducer 90. In certain embodiments, FUS transducer 110 may be round or annular and delivered ultrasound beam 140 may be conical. Angle α may be selected so that energy beam 140 is transmitted into the targeted area on the vertebra and does not penetrate the vertebra protrusions and lamina. Angle α may be selected to allow the incidence angle relative to the bone surface to be greater than the refraction angle, so that most of the energy is absorbed by the bone and not refracted. Optionally, angulation of device 100 and projected energy 140 may be used to optimize the incidence angle of the acoustic energy with respect to the bone to maximize absorption of energy by the bone.

Supporting structure 115 may be configured to keep transducers 110, 90 at their relative positions, and possibly to enable position adjustment between transducers 110, 90 and possibly replacement of transducer 90. Supporting structure 115 may comprise handle 116 and may support additional elements such as a trigger 119, display 120 and processing elements such as controller 160 and/or imaging unit 180. One or more controllers 160 and/or 180 may be configured to process image data from imaging transducer 90 and provide it to display 120 and to enable controlling FUS transducer 110, e.g., by trigger 119.

In certain embodiments, the location of the ultrasound imaging probe may be calibrated prior to treatment and the treatment location may be verified, e.g., by using FUS transducer 110 to sonicate a phantom to produce a bubble, imaging the location of the bubble, and adjusting displayed focal spot location 141 on the treatment image accordingly. In particular, the alignment of central axis 112 with respect to the image plane (e.g., aligning device 100 with central axis 112 so that the imaging plane of the ultrasound imaging probe would go through the middle of the acoustic focal point) may be calibrated prior to the application of the treatment. For example, device 100 may be used to sonicate a gel pad, create thereby a small bubble in the gel and images the bubble location may be taken imaging unit 180 to allow calculating the location of the focal spot in the ultrasound imaging plane. Alternatively or complementarily, a low level energy beam transmission may be applied by FUS transducer 110 at the beginning of the treatment to verify the targeting of the treatment by raising the target temperature of the tissue at the focal spot to a non-destructive level and monitor patient feedback and/or to detect tissue changes in the imaging. The resulting low temperature rise may trigger a neural response from the patient that may be used to verify the treatment location, or a lack of response may indicate a false focal point. Tissue heating may be visible on ultrasound and/or other imaging and be used to indicate the focal point of beam 140 just prior to the commencement of treatment. It is noted that calibration and/or low energy delivery may be carried out at any time during the treatment.

FIG. 3B schematically illustrates conceptual configurations of system 101. Supporting structure 115 in device 100 may comprise a recess or a socket 118 configured to receive imaging transducer 90 and enable positional adjustment and/or replacement thereof. Recess or socket 118 may be sized and shaped to surround and retain imaging transducer 90 in a fixed position. Recess or socket 118 may have a specified symmetry selected to receive one or more types of prior art imaging transducers 90. For example, recess or socket 118 may be round or square, and may have a rim configured to receive and hold imaging transducer 90.

Supporting structure 115 and/or device 100 may further comprise a shutter 117 configured to protect imaging transducer 90 during the operation of FUS transducer 110. For example, shutter 117 may be made of an ultrasound blocking (mechanically opaque, or ultrasound dampening) material. In certain embodiments, shutter 117 may be a leaf type shutter located in an acoustically transparent medium, e.g., as a coin shaped disk, filled with water and positioned between imaging probe 90 and coupling member 130 and/or patient's skin 83.

Controller 160 may be connected to a computer interface 124 communicating with external modules to provide operational parameters and control. For example, a computer 161 may comprise a device interface 164 communicating with computer interface 124 on device 100, a processing unit 162, a user interface 163 optionally communicating with a display 185 and a network interface 165 communicating with imaging unit 180, e.g., via a network interface 181 therein.

Imaging transducer 90 may be connected to external modules providing image processing. Imaging unit 180 may communicate via a probe interface 182 with imaging transducer 90 and receive image data therefrom, and possibly communicate via a user interface 183 with a user. In certain embodiment, processing unit 162 may comprise an image receiving module 171 (e.g., communicating with imaging unit 180), a display module 172 (e.g., communicating with user interface 163) and a guiding module 173 configured e.g., to relate focused ultrasound application with image data and possibly to suggest and/or control the delivery of focused ultrasound energy. Imaging unit 180 may be configured to process images received from imaging transducer 90, e.g., to identify the location of skin 83 and of other anatomical elements on images taken at angle α. Markers on skin 83 may be used to calibrate and register the displayed images.

Imaging unit 180 may be configured to detect hyperechoic signals associated with tissue heating and cavitation, generated when rapid tissue heating gets to a boiling level or when a sharp pressure changes creates bubbles at the acoustic energy focal point (cavitation). The hyperechoic signals and/or their harmonics may serve to provide feedback to the user on the effect of the energy delivery on the tissue. Imaging unit 180 may be configured to implement image processing algorithms to detect and visualize nerve branch anatomy by itself and/or with respect to the vertebra processes, at different imaging planes and/or as a three dimensional model.

Processing unit 162 may be configured to calculate the focal spot, energy beam locations and related energy delivery parameters according to the treatment image and to indicate and guide the positioning and maneuvering of device 100 to enable focused ultrasound delivery according to the calculated parameters. Processing unit 162 may be configured to calculating positioning accuracies and provide feedback on the advancement of the treatment according to intermittent images taken during the treatment. Processing unit 162 may be configured to display on the two dimensional image various three dimensional imaging data to enable effective positioning and treatment application. Processing unit 162 and/or controller 160 may be configured to provide three dimensional imaging and/or to follow multiple applications of focused ultrasound at multiple locations 141 with a three dimensional image or model of tissue 80. Controller 160 may be further configured to provide feedback to the user, e.g., as visual indications, auditory indications and/or haptic feedback indications (e.g., via handle 116). Visual indications may be displayed, e.g., as colored indications relating to different regions in the displayed image. In certain embodiments, processing unit 162 and/or controller 160 may be configured to override operator activation of FUS transducer 110, e.g., when FUS transducer 110 is focused at a wrong location (e.g., due to operator or patient's unexpected movements) or applied at a wrong intensity.

Processing unit 162 may comprise a software module running on a computerized processor and configured to receive a treatment image from imaging transducer 90, configured to send the treatment image to computerized display 120 (and/or display 185), and configured to mark a focal spot location of the ultrasound treatment beam on the computerized display over the treatment image. Any element of computer 161 may in certain embodiments incorporated into controller 160 and possibly operate from device 100.

System 101 may further comprise a safety sub-system 170 for monitoring and if necessary limiting ultrasound energy delivery according to measurements and predefined thresholds. Safety sub-system 170 may be configured to monitor the power being generated in real time (e.g., electronically) to avoid projecting too much power and/or safety sub-system 170 may be configured to monitor acoustic reflection level (e.g., using imaging transducer 90) to reduce the risk of skin burn that may be caused by improper acoustic coupling. Safety sub-system 170 may be configured to monitor the total energy output, improper acoustic coupling and/or changes in echogenicity of the target. Safety sub-system 170 may be configured to override operator activation of trigger 119.

Figure 4B:
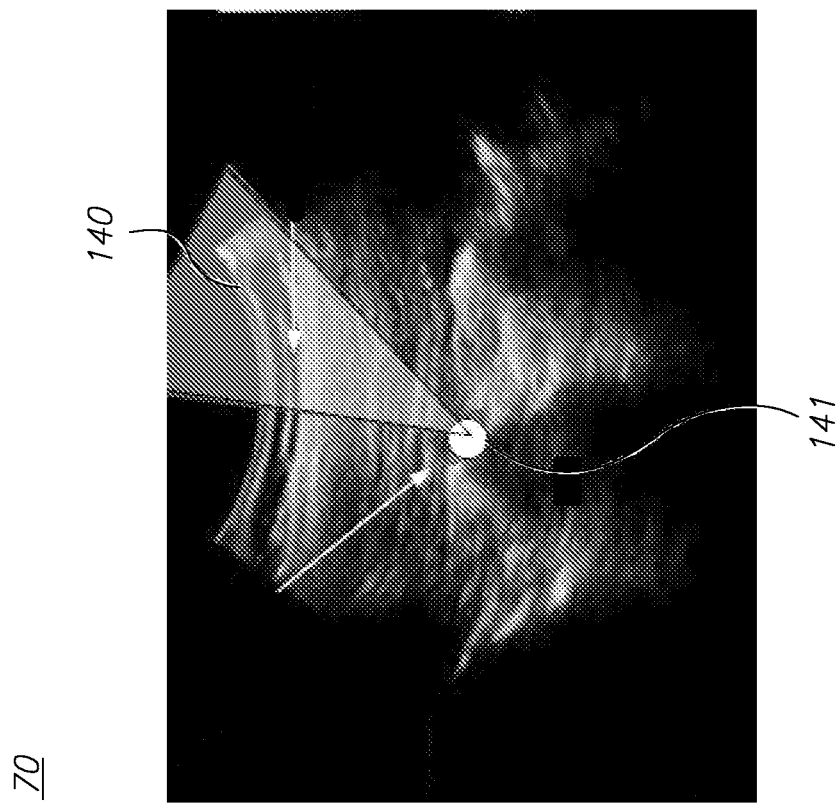
FIGS. 4A and 4B are schematic examples of ultrasound images and treatment application, according to some embodiments of the invention.
Figure 4A:
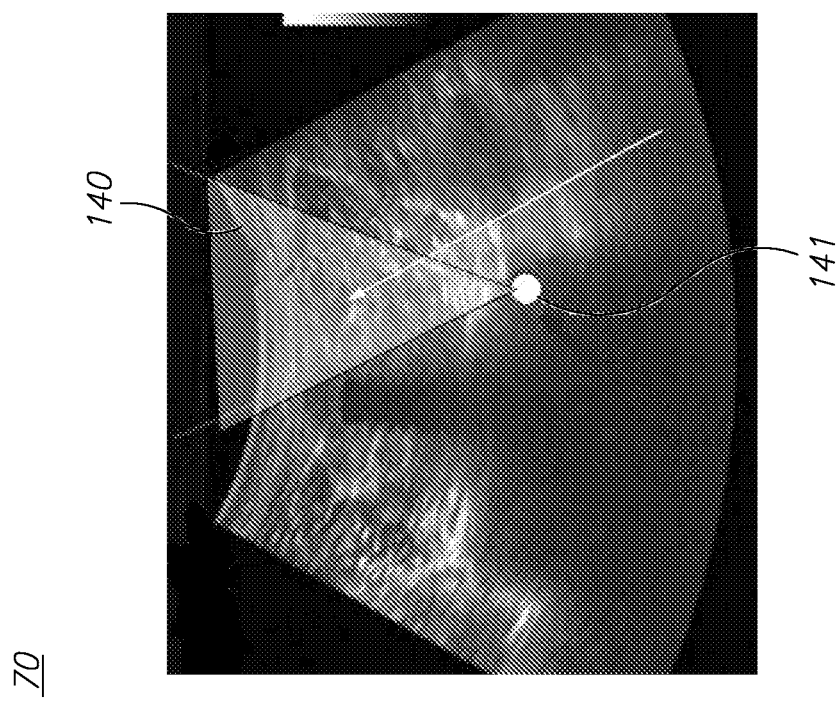

FIGS. 4A and 4B are schematic examples of ultrasound images 70 and treatment application, according to some embodiments of the invention. FIGS. 4A and 4B illustrate images 70 with overlaid designation of focused ultrasound beams 140 and treatment locations 141, which may represent actual compound images on display 120 and/or computation stages by controller 160 and/or processing unit 162.

Figure 5D:
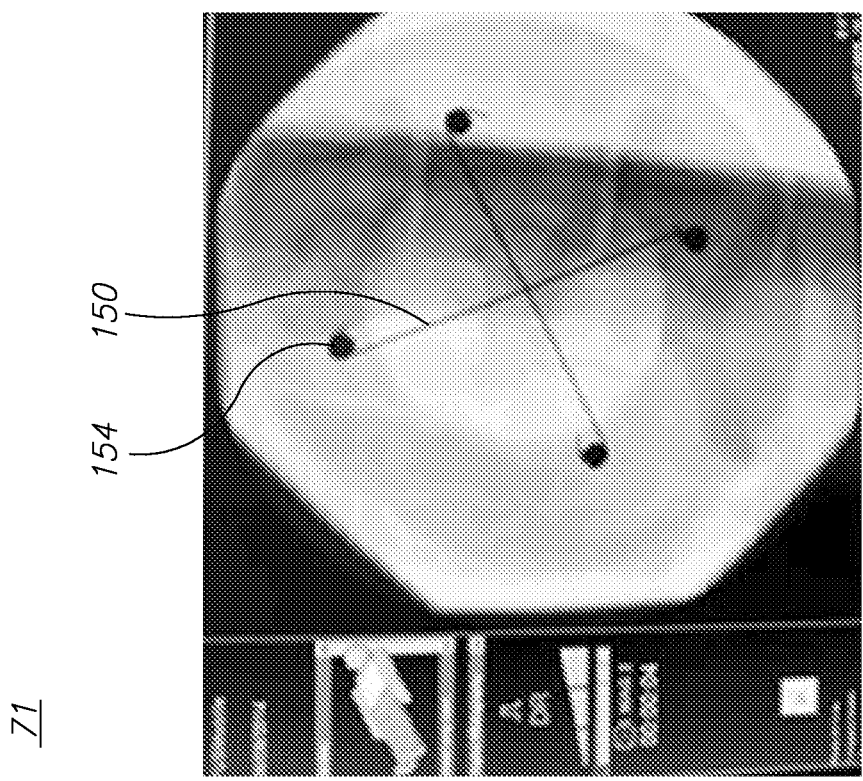
FIGS. 5A, 5A', 5B, 5B', 5C and 5D are schematic illustrations of a device with x-ray guidance, according to some embodiments of the invention.
Figure 5C:
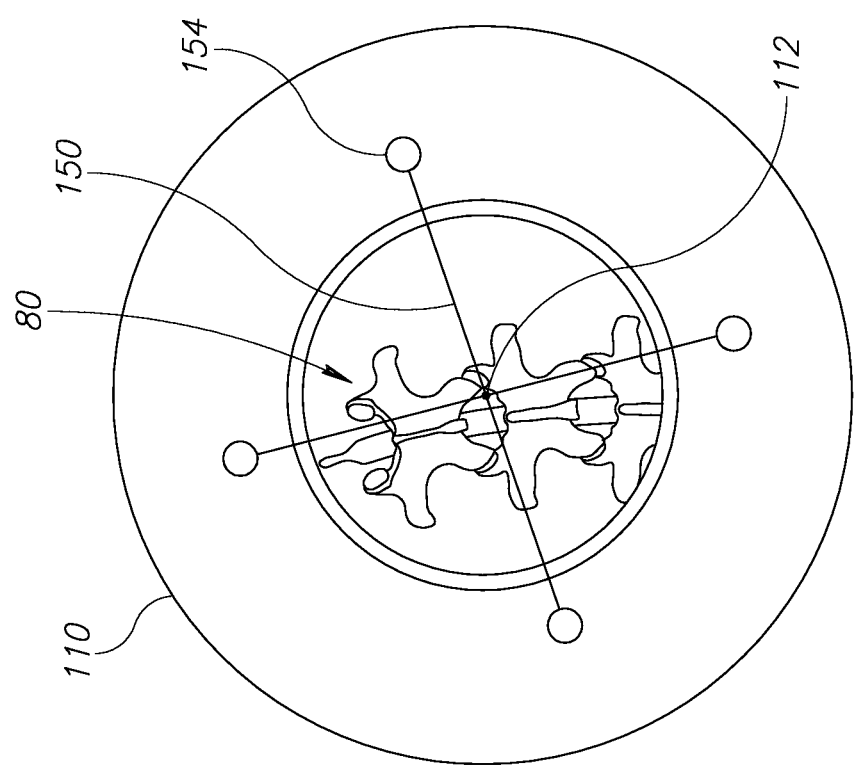

FIGS. 5A, 5A', 5B, 5B', 5C and 5D are schematic illustrations of device 500 with x-ray guidance, according to some embodiments of the invention. FIGS. 5A and 5A' and 5B and 5B' schematically illustrate x-ray aiming of the focused ultrasound and FIGS. 5C and 5D schematically exemplify treatment application by device 500. Device 500 may comprise supporting structure 515, focused ultrasound (FUS) transducer 110 having central axis 112 that is affixed to supporting structure 515, and an x-ray aim 150 comprising at least two parallel and congruent members 151, 152, e.g., cross-shaped members (such as fiducial wires) having their centers along central axis 112 of FUS transducer 110. It is noted that supporting structure 515 may be optionally configured similarly to supporting structure 115 illustrated in any of FIGS. 1A, 1B and 2, with x-ray aim 150 replacing ultrasound imaging transducer 90. For example, recess or socket 118 as illustrated in FIGS. 1B and/or 3B may be sized and shaped to surround and retain x-ray aim 150 in a fixed position. X-ray aim 150 may be attached to supporting structure 515 and/or directly to FUS transducer 110 along central axis 112 thereof. FUS transducer 110 may be connected to controller 160 that is configured to control application of focused ultrasound by transducer 110. FUS transducer 110 may be mechanically connected to supporting structure 515 in a way that sets a focal spot location of FUS transducer 110 along central axis 112 and in the center of x-ray aim 150. Imaging unit 580 in the illustrated embodiments may comprise an x-ray imaging system, as illustrated schematically in FIG. 5B. In certain embodiments, an arm 114 may be connected to supporting structure 515 to enable handling and manipulation of device 500 in x-ray imaging unit 580. Aligning members 151, 152 to an overlapping position (as illustrated in FIGS. 5B' and 5C-5D) indicates the direction of central axis 112 and enables positioning device 500 with axis 112 going through treatment location 141. X-ray aim 150 may further comprise framing elements 154 to assist in the positioning of x-ray aim 150 and in the identification of a proper alignment of members 151, 152, as illustrated in x-ray image 71 of FIG. 5D. X-ray image 71 and x-ray aim 150 may be calibrated using x-ray markers (not shown). The focal spot location of FUS transducer 110 may be calibrated with respect to the center of x-ray aim 150 in various ways, e.g., by software corrections, by hardware corrections, with respect to one or more reference images, with respect to an image with a sonicated reference imaging phantom (sonicated using FUS transducer to view its alignment with fiducial markers 151, 152) etc. Coupling member 530 may be used to position device 500 in a similar manner as explained above. Coupling member 530 may be transparent to x-ray in order not to interfere with the x-ray imaging.

In certain embodiments, supporting structure 515 may comprise handle 516 and may be associated with an imaging unit 580 configured to generate an x-ray image 71 of x-ray aim 150 on the patient's tissue. Supporting structure 515 may comprise recess or socket configured to receive x-ray aim 150 and enable positional adjustment thereof. The recess or socket may be sized and shaped to surround and retain x-ray aim 150 in a fixed position. Aim members 151, 152 may be made of an x-ray opaque material that is visible on an x-ray image of the treatment regions and allow verifying that members 151, 152 are aligned and hence that treatment location 141 is on central axis 112. In certain embodiments, kit 102 may comprise several sets of x-ray aims 150, having e.g., different types of members 151, 152 such as fiducials of different dimensions, different dimensions of aim 150 etc and or aims 150 having surfaces that are parallel to central axis 112, as illustrated e.g., in FIG. 6A (see below). Supporting structure 515 may be attached to the treatment table to allow stable positioning of transducer 110 under x-ray guidance, and thus avoid exposing the treating physician to x-ray radiation. Alternatively or complementary, arm 114 may be used to manipulate supporting structure 515 and/or device 500.

Controller 160 may be configured to apply focused ultrasound only upon coinciding of at least two parallel and congruent members 151, 152 on x-ray image 71. Thus, x-ray aim 150 provides geometric means to align FUS transducer 110 along the treatment line and enable applying focused ultrasound onto the treatment location.

In device 500 employing x-ray imaging (as in the ultrasound imaging device), supporting structure 515 may further comprise a display 120 that is connected to imaging unit 580 and configured to display the imaging data from imaging unit 580. It is noted that display 120 may be mounted on supporting structure 515 in a way that simplifies the aiming of focused ultrasound on targets that are imaged by imaging ultrasound transducer 90, and/or may be separate from supporting structure 515 and comprise e.g., a screen or a computer display that may be used by the operator to achieve higher magnifications and enable further processing. Combinations of mounted display 120 and separate display 120 are likewise embodiments of the present invention. In certain embodiments, device 500 may further comprise a mechanical shutter 117 (illustrated schematically by the broken line in FIG. 1B and in FIG. 3B) that is attached to supporting structure 515 in front of imaging transducer 90 and is configured to protect imaging transducer 90 during an operation of FUS transducer 110. Alternatively or complementarily, protection of imaging transducer 90 during an operation of FUS transducer 110 may be carried out electronically.

In certain embodiments, ultrasound imaging and x-ray imaging may be combined and used simultaneously or sequentially, and device 100 may comprise both ultrasound transducer 90 and x-ray aim 150. For example, x-ray imaging may be employed to clarify details in an ultrasound image of the treatment region and to provide more information to the user. In certain embodiments, the ultrasound image may be used to evaluate the depth of target 141 from therapeutic FUS transducer 110. X-ray aim 150 may be aligned with both transducers 110, 90 to enable registration of ultrasound image 70 and x-ray image 71 and/or registration of data from images 70, 71. Additional information sources may be combined (e.g., superimposed) with any of images 70, 71, such as CT (computed tomography) images, MRI (magnetic resonance imaging) images, fluoroscopy images or any other image. In certain embodiments, monitoring focused ultrasound treatment may be carried out with diagnostic elements separate from device and located at or within patient's tissue 80.

Figure 7B:
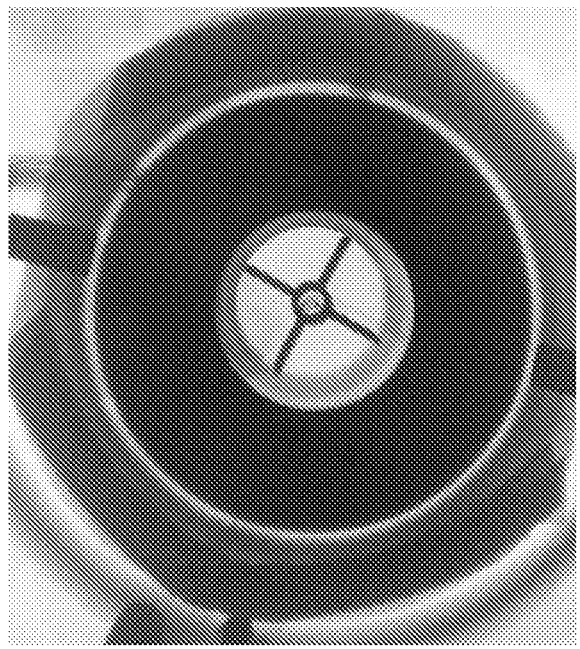
FIGS. 7A and 7B are x-ray-images of the x-ray aim at different positions, according to some embodiments of the invention.
Figure 7A:
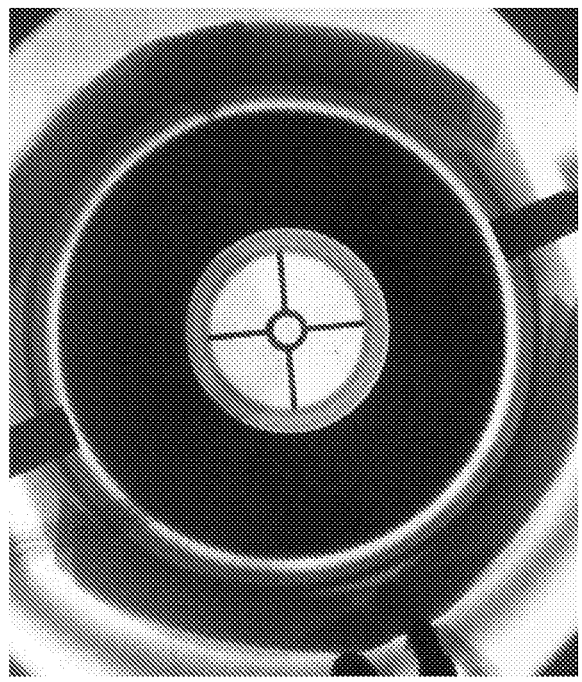

FIGS. 6A-6D are high level schematic illustrations of x-ray aim 150, according to some embodiments of the invention. FIGS. 6A and 6B are perspective views, FIG. 6C is a perspective cross section and FIG. 6D is a photograph of aim 150 and transducer 110. X-ray aim 150 may comprise a member 153 having surfaces along central axis 112 which appear as lines in images taken directly along central axis 112 but appear as surfaces in images taken at an angle (oblique) to central axis 112. Member 153 may be designed to achieve high sensitivity to small angles of inclination thereof from a line perpendicular to the image plane. FIGS. 7A and 7B are x-ray images of x-ray aim 150 at different positions, according to some embodiments of the invention. In FIG. 7A x-ray aim 150 and central axis 112 are exactly perpendicular to the image plane of image 156A, resulting in linear appearance (i.e., minimal width of the projections) of the surfaces of member 153. In contrast, in FIG. 7B x-ray aim 150 and central axis 112 are slightly inclined with respect to the normal to the image plane of image 156B and the surfaces of member 153 are accordingly somewhat blurred and wider than the minimal width of their linear appearance in FIG. 7A. Returning to FIGS. 6A-6D, member 153 is illustrated as a central cylinder 153A parallel to central line 112 and externally protruding surfaces 153B parallel to central line 112. It is noted that protruding surfaces 153B may differ from each other in dimensions that are perpendicular to central axis 112 in order to simplify orientation at the image plane (see images 156A, 156B in FIGS. 7A and 7B respectively). Alternatively or complementarily, one or more marking elements (not shown) may be attached to x-ray aim 150 to indicate the orientation of x-ray aim 150 in the image plane.

In certain embodiments, x-ray aim 150 may be asymmetric in the image plane (e.g., surfaces 153B may have different lengths or different forms in the image plane) to indicate the orientation of x-ray aim 150 in the image plane. In certain embodiments, x-ray aim 150 may comprise multiple cylinders 153A (appearing as rings in an image plane that is perpendicular to central axis 112), possibly concentric cylinders having different diameters. Any part of x-ray aim 150 and/or member 153 may be configured to provide depth information in the x-ray image with respect to the central axis. For example, surfaces 153B may extend to different depths along central axis 112 (in slanted view) and/or may comprise elements protruding therefrom into the image plane.

Supporting structure 115 may be configured to affix along common central axis 112 FUS transducer 110 and imaging ultrasound transducer 90, and enable replacement of the latter; and/or supporting structure 515 may be configured to affix along common central axis 112 FUS transducer 110 and x-ray aim 150, and further comprise arm 516 configured to enable manipulating supporting structure 515 during x-ray imaging thereof.

Figure 8A:
FIG. 8A is a high level schematic illustration of a treatment location, according to some embodiments of the invention.
Figure 8B:
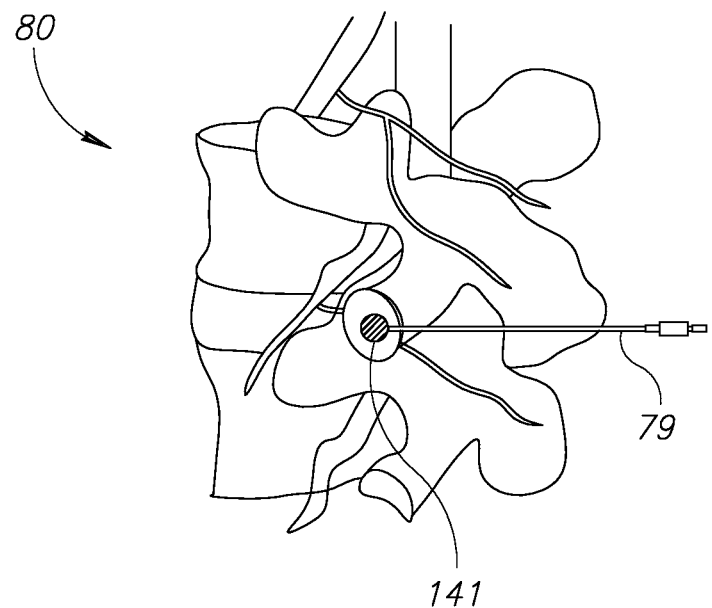
FIG. 8B is a high level schematic illustration of a prior art treatment.

FIG. 8A is a high level schematic illustration of a treatment location 141, according to some embodiments of the invention. Treatment location 141 is relevant for facet rhizotomy as a non-limiting example FIG. 8B is a high level schematic illustration of a prior art treatment. FIG. 8B illustrates the prior art invasive procedure of inserting an electrode 79 to treatment location 141 to ablate or sever the respective nerve branch using electromagnetic radiation (e.g., radiofrequency (RF) radiation or laser). In contrast, focused ultrasound treatment as illustrated in FIG. 8A merely aims beam 140 in a non-invasive manner to treatment location 141 in order to cause the corresponding effect. Moreover, the aiming procedures disclosed herein, using either or both ultrasound imaging and x-ray imaging, which are aligned with FUS transducer 110, enable exact aiming of beam 140, avoiding chirurgical procedures and avoid damage to surrounding tissues. Moreover, an imaging unit (e.g., the imaging unit 180 or 580 of FIGS. 1A and 5B, respectively) may be configured to automatically detect movements of a device (e.g., the device 100 of FIGS. 1A and 1B or device 500 of FIGS. 5A and 5B) and/or of the patient and prevent unintended damage due thereto. For example, movement detection may be based on the vertebra bone surface delineation as illustrated in FIG. 8A, that may result from the image processing. Alternatively or complementarily, a controller (e.g., the controller 160 of FIG. 1A or FIGS. 5A' and 5B') may be configured to automatically compensate for certain movements, adjusting the focal point of beam 140 to remain at treatment location 141 during and after the detected movements.

Figure 9:
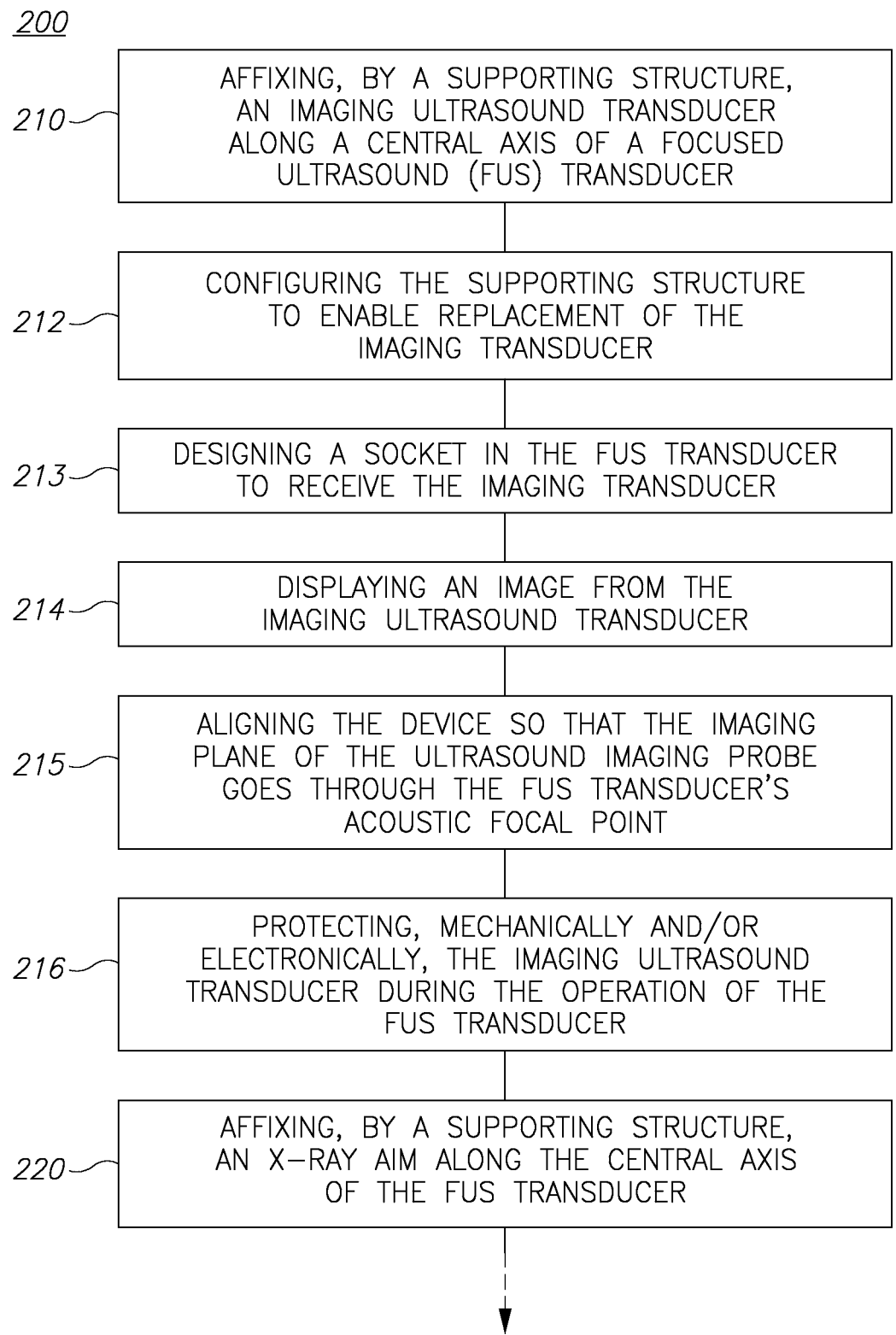
FIG. 9 is a high level flowchart illustrating a method, according to some embodiments of the invention.

FIG. 9 is a high level flowchart illustrating a method 200, according to some embodiments of the invention.

In certain embodiments, method 200 may comprise affixing, by a supporting structure, an imaging ultrasound transducer along a central axis of a focused ultrasound (FUS) transducer (stage 210). Method 200 may further comprise configuring the supporting structure to enable replacement of the imaging transducer (stage 212), for example, method 200 may comprise designing a socket in the FUS transducer to receive the imaging transducer (stage 213). Method 200 may further comprise displaying an image from the imaging ultrasound transducer (stage 214), aligning the device so that the imaging plane of the ultrasound imaging probe goes through the FUS transducer's acoustic focal point (stage 215) and possibly protecting, mechanically and/or electronically, the imaging ultrasound transducer during the operation of the FUS transducer (stage 216).

In certain embodiments, method 200 may comprise affixing, by a supporting structure and along a central axis of a focused ultrasound (FUS) transducer, an x-ray aim (stage 220). It is noted that using an imaging transducer and using an x-ray aim may be alternative method steps and other stages apply to the respective alternative when applicable.

Method 200 may comprise configuring the x-ray aim to indicate, visually upon an x-ray image thereof, an inclination of the x-ray image with respect to the central axis (stage 225). The visual indication may relate to any image feature that may indicate the inclination of the x-ray aim with respect to the image plane, and particularly to indicate a perpendicular position of the x-ray aim (and the device) to the image plain. For example, sharpness, dimensions and/or form of the x-ray aim in the image may be used as visual indications.

In certain embodiments, method 200 may comprise designing the x-ray aim to comprise one or more surface(s) and/or one or more cylinder(s) parallel to the central axis of the FUS transducer (stage 230), e.g., at least two mutually perpendicular surfaces, one or more concentric cylinders etc., possibly having different lengths along the central axis and/or marking element(s) attached to any part of the x-ray aim to ease adjusting the x-ray aim and the device according to obtained x-ray image(s).

The x-ray aim may be designed to comprise at least two parallel and congruent members (stage 232), and method 200 may further comprise enabling application of focused ultrasound by the FUS transducer only upon coinciding of the parallel and congruent members on a corresponding x-ray image.

Method 200 may further comprise x-ray imaging a target with the supporting structure and the x-ray aim (stage 235) and optionally displaying the x-ray image (stage 237). In certain embodiments, method 200 may comprise enabling application of focused ultrasound only upon indication that the x-ray image is perpendicular to the central axis (stage 238).

In certain embodiments, method 200 may comprise coupling the FUS transducer with a target at a specified angle of the central axis with respect to a patient's skin above the target (stage 240).

Method 200 may further comprise controlling application of focused ultrasound by the FUS transducer according to the displayed image (stage 250), be it imaging ultrasound image and/or x-ray image.

Any of the ultrasound and/or x-ray image(s) may be processed and enhanced, e.g., (i) by delineating bones on the image, (ii) by registering bones according to an anatomical atlas and/or a patient CT, MRI, fluoroscopy or any other image, and/or (iii) by suggesting treatment location and/or approach angle α—to ease orientation of the operator and improve the application of the treatment by focused ultrasound. Method 200 may comprise enhancing any of the images with anatomical and treatment related information (stage 252).

In certain embodiments, devices 100, systems 101, kits 102 and methods 200 may be used in facet rhizotomy to treat medial branch nerves. For example, device 100 may be configured as a mobile, handheld, low-cost device for projecting non-invasive focused ultrasound energy to the treatment location (e.g., to cause thermal ablation of respective nerves), according to concurrent ultrasound and/or x-ray imaging, as described above. Application of focused ultrasound may be carried out to achieve any of a number of effects, such as heating, thermal destruction of tissue, mechanical effects, cavitation etc., in a non-invasive manner. It is noted that thermal effects on the treatment location 141 may be achieved by direct heating or by indirect heating with beam 140 aimed at adjacent bone material that is heated to a level that damages the respective nerve. Treatment with focused ultrasound may achieve additional goals, such as treating various pains, treating clots or other specific tissues, ablating tumors, enhancing drug delivery etc., and may be enhanced by injected fluids which modify acoustic tissue absorption. The concurrent imaging may ease the approach to the treatment location, ensure correct aiming of the focused ultrasound energy and enable viewing the treatment location within the image during treatment. Multiple treatment locations may treated with focus ultrasound sequentially, utilizing intermittent imaging to control the advancement of the treatment. In certain embodiments, device 100 may be used as a general purpose tissue ablation device.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A device for a focused ultrasound (FUS) treatment of a tissue, the device comprising:
    a supporting structure comprising an arm configured to enable manipulating the supporting structure with respect to an X-ray imaging unit,
    a FUS transducer having a central axis that is affixed to the supporting structure, and
    an x-ray aim attached to the supporting structure and directly to the FUS transducer along the central axis of the FUS transducer,
    wherein the FUS transducer is connected to a controller configured to control application of focused ultrasound energy by the FUS transducer.

2. The device of claim 1, wherein the x-ray aim comprises a central cylinder which is parallel to the central axis of the FUS transducer.

3. The device of claim 2, wherein the x-ray aim further comprises at least one surface externally protruding from the central cylinder parallel to the central axis of the FUS transducer.

4. The device of claim 3, wherein the x-ray aim comprises at least two surfaces externally protruding from the central cylinder parallel to the central axis of the FUS transducer, wherein the at least two surfaces differ from each other in dimensions that are perpendicular to the central axis of the FUS transducer.

5. The device of claim 1, associated with the X-Ray imaging unit configured to generate an x-ray image of the x-ray aim.

6. The device of claim 5, wherein the controller is configured to apply focused ultrasound only upon identification, using imaged features of the x-ray aim, of a perpendicular orientation of the x-ray image to the central axis.

7. The device of claim 1, further comprising a coupling member configured to couple the FUS transducer with a target at a specified angle with respect to the central axis of the FUS transducer.

8. The device of claim 1, wherein the x-ray aim further comprises at least one marking element attached to at least one of the at least one surface.

9. The device of claim 1, wherein the x-ray aim comprises at least two parallel and congruent members having their centers along the central axis of the FUS transducer.

10. The device of claim 9, wherein the controller is configured to apply focused ultrasound only upon coinciding of the at least two parallel and congruent members on the x-ray image.

* * * * *